United States Patent
Huc et al.

(10) Patent No.: US 9,809,523 B2
(45) Date of Patent: Nov. 7, 2017

(54) PROCESS FOR THE HIGH-YIELD PREPARATION OF P-(R)CALIX[9-20]ARENES

(71) Applicants: UNIVERSITE PARIS-SUD XI, Orsay (FR); CENTRE NATIONAL DE LA RECHERCHE SCIENTIFIQUE, Paris (FR)

(72) Inventors: Vincent Germain Huc, Orsay (FR); Cyril Martini, Bures sur Yvette (FR)

(73) Assignees: UNIVERSITE PARIS-SUD XI, Orsay (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/122,324

(22) PCT Filed: Feb. 27, 2015

(86) PCT No.: PCT/FR2015/050479
§ 371 (c)(1),
(2) Date: Aug. 29, 2016

(87) PCT Pub. No.: WO2015/128593
PCT Pub. Date: Sep. 3, 2015

(65) Prior Publication Data
US 2016/0368849 A1    Dec. 22, 2016

(30) Foreign Application Priority Data
Feb. 28, 2014 (FR) .................................... 14 51660

(51) Int. Cl.
C07C 41/30 (2006.01)
C07C 41/34 (2006.01)
C08G 8/00 (2006.01)
C07C 67/14 (2006.01)
C07C 41/40 (2006.01)
C08G 8/20 (2006.01)
C08G 8/28 (2006.01)
C08G 83/00 (2006.01)

(52) U.S. Cl.
CPC ............. *C07C 41/30* (2013.01); *C07C 41/34* (2013.01); *C07C 41/40* (2013.01); *C07C 67/14* (2013.01); *C08G 8/20* (2013.01); *C08G 8/28* (2013.01); *C08G 83/005* (2013.01); *C07C 2603/92* (2017.05); *C08G 2105/00* (2013.01)

(58) Field of Classification Search
CPC ............ C07C 41/30; C07C 41/34; C08G 8/20
See application file for complete search history.

(56) References Cited

U.S. PATENT DOCUMENTS

2015/0011798 A1    1/2015  Huc et al.

FOREIGN PATENT DOCUMENTS

| CA | 2251070 A1 | 10/1997 |
| WO | WO97/37957 | * 10/1997 |
| WO | 2013/088056 A1 | 6/2013 |

OTHER PUBLICATIONS

Casnati et al. p-(Benzyloxy) calix[8] arene: One-Pot Synthesis and Functionalization. Journal of Organic Chemistry, 1997, vol. 62, 6236-6239.*
International Search Report, dated Jul. 3, 2015, from corresponding PCT Application.

* cited by examiner

*Primary Examiner* — Sikarl Witherspoon
(74) *Attorney, Agent, or Firm* — Young & Thompson

(57) ABSTRACT

A process for the high-yield preparation of p-(R)calix[9-20] arenes.

17 Claims, No Drawings

PROCESS FOR THE HIGH-YIELD PREPARATION OF P-(R)CALIX[9-20]ARENES

The present invention relates to a process for the high-yield preparation of p-(R)calix[9-20]arenes.

The calixarenes have been the subject of particular study in the last thirty years owing to the immense possibilities offered by these easily accessible macrocycles. These macrocycles are cup-shaped, the cavity generally being less than or equal to approximately 1 nm.

Some of the properties most studied include the phenomena of recognition of the inorganic ions and organic molecules, the supramolecular assemblies or also the synthesis of nanoparticles, among other things.

In most cases, these studies were carried out with calixarenes functionalized with a p-(t-butyl) or with calixarenes obtained by chemical modification of these p-(t-butyl)calixarenes, since the synthesis of p-(t-butyl)calixarenes is by far the most documented since the pioneering work of Gutsche et al. D. Gutsche, *Calixarenes: An Introduction*, The Royal Society of Chemistry, Cambridge, 2008. Z. Asfari, V. Böhmer, J. Harrowfield, J. Vicens, *Calixarenes* 2001, Kluwer, Dordrecht, the Netherlands, 2001.

Consequently, the use of other monomers of the functionalized phenol type for the synthesis of calixarenes is largely unexplored, even if one-stage syntheses of other p-(alkyl) calixarenes are known (T. Patrick, P. Egan, *J. Org. Chem.* 1977, 42, 382; T. Patrick, P. Egan, *J. Org. Chem.* 1978, 43, 4280; Z. Asfari, J. Vicens, *Tetrahedron Lett.* 1988, 29, 2659; F. Vocanson, M. Perrin, R. Lamartine, *J. Inclusion Phenom. Macrocyclic Chem.* 2001, 39, 127; Jerry L. Atwood et al; *Org. Lett.* 1999, 1, 1523).

The p-substituted calixarenes are usually obtained in a mixture of p-calix[4, 5, 6, 7, 8]arenes by reaction of a p-substituted phenol with paraformaldehyde in the presence of at least one base such as potassium hydroxide or sodium hydroxide (B. Dahwan et al., *Macromolec. Chem.* 1987, 188, 921; C. D. Gutsche et al., *Org. Synth.* 1990, 68, 234; C. D. Gutsche et al., *Org. Synth.* 1990, 68, 238).

In most cases, withdrawal or substitution of the hydroxyl function of these calixarenes from the alkyl groups to para, when it is possible, is at best difficult. In the commonest case of the p-(t-butyl)calixarenes, it is generally a multi-stage process. Firstly, a reagent of the Lewis acid type is generally combined with a phenol to remove the t-butyl group. Secondly, another function may be introduced in place of the t-butyl group, by electrophilic substitution. As the reaction is not quantitative, "deterbutylation" becomes problematic, in particular when the number of calixarene units increases. The presence of by-products limits the yield, makes a purification stage necessary and restricts the purity of the product. This may limit the final yield of fully deprotected product, as well as the use thereof.

The p-(benzyloxy)calixarenes represent a very useful alternative to the p-(alkyl)calixarenes. The (benzyloxy)phenol units are in fact reduced quantitatively to phenols by hydrogenolysis catalysed by palladium on charcoal, allowing easy post-functionalization.

Few documents describe the synthesis of large calixarenes, i.e. comprising from 9 to 20 repeat units.

Thus patent CA 2,251,070 describes the production of calixarenes comprising 9 and 11-14 repeat units with low yields, by a two-stage process by reaction of a p-(alkyl) or p-(aralkyl)phenol in an aqueous medium in the presence of a base in a quantity of less than 0.5 eq and then heating in an organic solvent without water.

This patent does not describe the production of p-(R-oxy)calix[9-20]arenes.

The article by Gutsche et al. (*J. Am. Chem. Soc.* 1999, 121, 4136) only describes the production of p-(t-butyl)calix[9-20]arenes in an acid medium but not, in particular, the production of p-(R-oxy)calixarenes.

Consequently, it remains an open question as to how to obtain large calixarenes that can be easily functionalized on the high crown with a large variety of chemical groups under mild conditions and, in particular, how to obtain large calixarenes such as the p-(R)calix[9-20]arenes, in particular the p-(R-oxy)calix[9-20]arenes with good yields.

One of the aims of the invention is the manufacture of p-(R)calix[9-20]arenes, in particular p-(R-oxy)calix[9-20] arenes with cumulative yields greater than 5%, in particular greater than 10, 15, 20, 25, 30, 35, 40, 45 or 50%.

One of the aims of the invention is the manufacture of p-(R)calix[9-12]arenes, in particular p-(R-oxy)calix[9-12] arenes with cumulative yields greater than 5%, in particular greater than 10, 15, 20, 25, or 30%.

Another aim of the invention is to provide a synthesis process making it possible to obtain a mixture of twelve p-(R)calix[9-20]arenes, in particular of twelve p-(R-oxy) calix[9-20]arenes, or of a few p-(R)calix[9-20]arenes, in particular of a few p-(R-oxy)calix[9-20]arenes, isolated and pure, or a mixture of two, three, four, five, six, seven, eight, nine, ten or eleven out of the twelve, as well as a purification procedure making it possible to obtain them pure, in particular free from giant p-(R)calixarenes, the size of which is greater than 20, i.e. p-(R)calixarenes comprising more than 20 repeat units.

Another aim of the invention is to provide a synthesis process making it possible to obtain a mixture of four p-(R)calix[9-12]arenes, in particular of four p-(R-oxy)calix [9-12]arenes, or of a few p-(R)calix[9-12]arenes, in particular of a few p-(R-oxy)calix[9-12]arenes, isolated and pure, or a mixture of two or three out of the four, as well as a purification procedure making it possible to obtain them pure, in particular free from giant p-(R)calixarenes, the size of which is greater than 20, i.e. p-(R)calixarenes comprising more than 20 repeat units.

The present invention thus relates to a process for the preparation of:
  a large p-(R)calixarene selected from a p-(R)calix[9] arene, a p-(R)calix[10]arene, a p-(R)calix[11]arene, a p-(R)calix[12]arene, a p-(R)calix[13]arene, a p-(R) calix[14]arene, a p-(R)calix[15]arene, a p-(R)calix[16] arene, a p-(R)calix[17]arene, a p-(R)calix[18]arene, a p-(R)calix[19]arene, a p-(R)calix[20]arene, or
  a mixture of at least two of said large p-(R)calixarenes in which said at least two large p-(R)calixarenes are present in said mixture each at a level of at least 5 mol. %, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of the following formula (I):

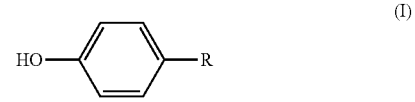

in which R is selected from:
- a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_1$-$C_{20}$ alkyl group, with the exclusion of the t-butyl group,
- a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_1$-$C_{20}$ alkyloxy group,
- a linear or branched 1 to 10 O-PEG group, the —OH end group of which is alkylated with a linear or branched $C_1$-$C_{20}$ alkyl,
- a benzyl thioether group —S—$CH_2$-Ph optionally substituted in the ortho and/or para and/or meta position with one or more substituents selected from a halogen, SR' and OR', $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_1$-$C_{20}$ alkyl thioether group, of formula —S—($C_1$-$C_{20}$-alkyl),
- an —$NR_aR_b$ group, $R_a$ and $R_b$ representing, independently of one another, a linear or branched $C_1$-$C_{20}$ alkyl,
- a dibenzylamine group of formula —N(benzyl)$_2$, in which the two benzyl groups are, independently of one another, optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl, and a source of aqueous formaldehyde,
in the absence or in the presence of an organic solvent, thus constituting an initial reaction medium,
said base being at a total concentration comprised from approximately 0.01 to 1 equivalent, in particular comprised from approximately 0.1 equivalent to approximately 0.4 equivalent, in particular equal to 0.15 or 0.4 equivalent or 1 equivalent, with respect to said at least one phenol substituted in position 4 of formula (I),
said initial reaction medium being heated to a temperature comprised from 100 to 165° C., in order to obtain a heated reaction medium,
and comprising, optionally, after said heating, a stage of additional heat treatment of said heated reaction medium, in the presence of heat transfer means, in particular an oven or a heated liquid.
in order to obtain a mixture (b), comprising said large p-(R)calixarene or said mixture (a) of at least two of said large p-(R)calixarenes, said mixture (b) comprising in addition a mixture (c) of giant p-(R)calixarenes, the size of which is greater than 20,
said process comprising moreover, after said heating and optional additional heat treatment, a stage of purification of said mixture (b), so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes.

Surprisingly, the Inventors noted the presence of large calixarenes in fractions that are usually discarded during the purification of reaction mixtures or residues comprising giant calixarenes.

Just as surprisingly, these large calixarenes have an original distribution of sizes with respect to those obtained by the processes for producing large calixarenes of the prior art.

By large p-(R)calixarene is meant a p-(R)calixarene selected from a p-(R)calix[9]arene, a p-(R)calix[10]arene, a p-(R)calix[11]arene, a p-(R)calix[12]arene, a p-(R)calix[13]arene, a p-(R)calix[14]arene, a p-(R)calix[15]arene, a p-(R)calix[16]arene, a p-(R)calix[17]arene, a p-(R)calix[18]arene, a p-(R)calix[19]arene and a p-(R)calix[20]arene.

By giant p-(R)calixarene is meant a p-(R)calixarene the size of which is greater than 20, i.e. a p-(R)calixarene comprising more than 20 repeat units. In other words, a giant p-(R)calixarene corresponds to a p-(R)calix[Z]arene, with Z>20.

By "devoid of said mixture (c) of giant p-(R)calixarenes" is meant that said large p-(R)calixarene or said mixture (a) of at least two of said large p-(R)calixarenes comprises less than 10% by mass of giant p-(R)calixarenes.

The term base denotes any base which is soluble in an aqueous medium of the metal hydroxide, tertiary amine, carbonate, sulphate, carboxylate type, for example.

It can also denote the use of an organic base of the amine type in combination with a metal salt (CsI for example).

The expression "source of aqueous formaldehyde" means that formaldehyde in an aqueous solution such as formalin or formol can be used.

The expression "in an aqueous solution" throughout the description means that the base is dissolved in a medium mainly consisting of water.

Advantageously, the expression "in an aqueous solution" denotes exclusively water.

The expression "in the absence or in the presence of an organic solvent" means that the reaction medium (which comprises water) is respectively devoid of or provided with solvents which are liquid organic compounds which contain carbon atoms, the base as such, the formaldehyde or source of formaldehyde and phenol also not being considered as an organic solvent.

The expression "reaction medium" means the mixture of the different components, comprising the base(s), the phenol(s) substituted in position 4 of formula (I), and the source of formaldehyde, all being in an aqueous solution or in a water-organic solvent medium.

When said mixture has just been constituted, it is called an initial reaction medium, i.e. a reaction medium in which the reaction for the preparation of the p-(R)calixarenes has not yet been carried out, in particular before any heating of said mixture of the different compounds.

The heated reaction medium corresponds to the initial reaction medium which has been heated to a temperature comprised from 100° C. to 165° C. for approximately 20 minutes to 5 hours.

When the reaction for the preparation of the giant p-(R)calixarenes is carried out, in particular after heating said mixture of the different compounds, and additional heat treatment, the reaction medium is then called the final reaction medium.

The expression "and then optionally subjected to an additional heat treatment in the presence of heat transfer means" means that after said heating at a temperature comprised from 100° C., to 165° C., during which water is optionally removed, heat transfer means are applied to the reaction medium, then said reaction medium is heated again.

The heat transfer means are in particular an oven or a heated liquid, in particular a liquid heated at a temperature comprised from 100° C. to 165° C., for example a liquid the boiling point of which is comprised from 100° C. to 165° C.

By liquid is meant a liquid, in particular a silicone oil or an organic liquid, more particularly an aromatic solvent or a linear or branched alkane, having a boiling point greater than 50° C., in particular greater than 100° C., in which said reaction medium or said solid precursor is only slightly soluble or totally insoluble, said liquid not reacting with said precursor.

By only slightly soluble is meant a solubility greater than or equal to $0.01$ g·L$^{-1}$, but less than $1$ g·L$^{-1}$.

By totally insoluble is meant a solubility less than $0.01$ g·L$^{-1}$.

By "liquid in which said reaction medium or said solid precursor is only slightly soluble" is therefore meant a liquid capable of optionally, according to its nature, partially solubilizing some of the constituents of said reaction medium, dispersing them (in order to form a colloidal suspension), or making all or part of them pass to a state of gel.

Thus, when the heat transfer means are for example an oven or a liquid in which the organic compounds of the reaction medium are only slightly soluble or totally insoluble, said additional heat treatment takes place in a solid phase, preferably without stirring.

In another advantageous embodiment, the reaction medium is devoid of organic solvent.

The initial reaction medium is thus heated in the absence of organic solvent, the base as such, the formaldehyde or the source of formaldehyde and phenol also not being considered as organic solvents.

The expression "reaction medium" therefore means the mixture of the different components, comprising the base(s), the phenol(s) substituted in position 4 of formula (I), the source of formaldehyde, all being in an aqueous solution.

In another advantageous embodiment, the reaction medium is devoid of organic solvent, the water is removed during said heating at a temperature comprised from 100 to 165° C., and said additional heat treatment is carried out in the presence of heat transmission means.

In another advantageous embodiment, the reaction medium is devoid of organic solvent, the water is not removed during said heating at a temperature comprised from 100 to 165° C., and said additional heat treatment is carried out in the presence of heat transmission means.

In another advantageous embodiment, the reaction medium comprises, besides water, an organic solvent, the water is not removed during heating, and said reaction medium is not subjected to said additional heat treatment.

In another advantageous embodiment, the reaction medium comprises, besides water, an organic solvent, the water is not removed during heating, and said reaction medium is subjected to said additional heat treatment, the water being in particular removed during said additional heat treatment.

The water-organic solvent system is capable of promoting solubilization of all of the organic and inorganic compounds, at the start of the reaction. This therefore makes it possible to maintain the constituents of the reaction medium for longer in solution. This results in a better consumption of the reagents, which leads to 1) a better yield, and 2) less by-products (starting products, reaction intermediates etc.). This makes purification easier.

The process of the invention makes it possible in particular to obtain a distribution of large p-(R)calix[9-12]arenes of interest.

In an advantageous embodiment, the present invention relates to a process for the preparation of:
 a large p-(R)calixarene selected from a p-(R)calix[9]arene, a p-(R)calix[10]arene, a p-(R)calix[11]arene, a p-(R)calix[12]arene, or
 a mixture (a) of at least two of said large p-(R)calixarenes in which said at least two large p-(R)calixarenes are present in said mixture each at a level of at least 5 mol. %.

The process of the invention makes it possible in particular to obtain large p-(alkyloxy)calix[9-20]arenes, p-(benzyloxy)calix[9-20]arenes or p-(PEG-oxy)calix[9-20]arenes.

In an advantageous embodiment, the present invention relates to a process for the preparation of:
 a large p-($R_1$-oxy)calixarene selected from a p-($R_1$-oxy)calix[9]arene, a p-($R_1$-oxy)calix[10]arene, a p-($R_1$-oxy)calix[11]arene, a p-($R_1$-oxy)calix[12]arene, a p-($R_1$-oxy)calix[13]arene, a p-($R_1$-oxy)calix[14]arene, a p-($R_1$-oxy)calix[15]arene, a p-($R_1$-oxy)calix[16]arene, a p-($R_1$-oxy)calix[17]arene, a p-($R_1$-oxy)calix[18]arene, a p-($R_1$-oxy)calix[19]arene, a p-($R_1$-oxy)calix[20]arene, or
 a mixture of at least two of said large p-($R_1$-oxy)calixarenes in which said at least two large p-($R_1$-oxy)calixarenes are present in said mixture each at a level of at least 5 mol. %, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of the following formula (Ia):

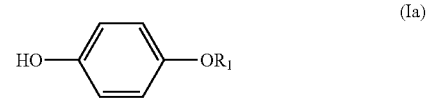

(Ia)

in which $R_1$ is selected from:
 a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
 a linear or branched $C_1$-$C_{20}$ alkyl group,
 a linear or branched PEG-1 to 10, the —OH end group of which is alkylated with a linear or branched $C_1$-$C_{20}$ alkyl,
 and a source of aqueous formaldehyde,
 in the absence or in the presence of an organic solvent, thus constituting an initial reaction medium,
 said base being at a total concentration comprised from approximately 0.01 to 1 equivalent, in particular comprised from approximately 0.1 equivalent to approximately 0.4 equivalent, in particular equal to 0.15 or 0.4 equivalent or 1 equivalent, with respect to said at least one phenol substituted in position 4 of formula (I), said initial reaction medium being heated to a temperature comprised from 100 to 165° C., in order to obtain a heated reaction medium, and comprising, optionally, after said heating, a stage of additional heat treatment of said heated reaction medium, in the presence of heat transfer means, in particular an oven or a heated liquid, in order to obtain a mixture (b), comprising said large p-($R_1$-oxy)calixarene or said mixture (a) of at least two of said large p-($R_1$-oxy)calixarenes, said mixture (b) comprising in addition a mixture (c) of giant p-($R_1$-oxy)calixarenes, the size of which is greater than 20, said process comprising moreover, after said heating and optional additional heat treatment, a stage of purification of said mixture (b), so as to remove said mixture (c) of giant p-($R_1$-oxy)calixarenes, and to obtain said large p-($R_1$-oxy)calixarene or said mixture (a) of at least two of said large p-($R_1$-oxy)calixarenes, devoid of said mixture (c) of giant p-($R_1$-oxy)calixarenes.

The process of the invention makes it possible in particular to obtain a distribution of large p-($R_1$-oxy)calix[9-12] arenes of interest.

In an advantageous embodiment, the present invention relates to a process for the preparation of:

a large p-($R_1$-oxy)calixarene selected from a p-($R_1$-oxy) calix[9]arene, a p-($R_1$-oxy)calix[10]arene, a p-($R_1$-oxy)calix[11]arene, a p-($R_1$-oxy)calix[12]arene, or a mixture of at least two of said large p-($R_1$-oxy)calixarenes in which said at least two large p-($R_1$-oxy) calixarenes are present in said mixture each at a level of at least 5 mol. %, In the process according to the invention, the initial reaction medium comprises water, in particular contributed by the source of aqueous formaldehyde. Moreover, water is formed during the reaction of formation of the calixarenes.

The water present in the initial reaction medium, as well as that produced during the reaction can be removed from said reaction medium during said heating.

In an advantageous embodiment, the present invention relates to a process in which the water present in the initial reaction medium, as well as that produced during the reaction are removed from said reaction medium during said heating and a solid precursor in the form of an optionally isolated, hard brittle resin is obtained.

Said solid precursor in the form of hard brittle resin is in particular obtained by heating the reaction medium at a temperature comprised from 100 à 165° C. for a time comprised from 1 to 5 hours, while optionally removing the water present in the initial reaction medium as well as that formed during the course of the reaction.

Advantageously, the heating is at approximately 110° C., 120° C., 130° C., 140° C., 150° C. or 160° C.

In this case, the proportion of the water present after the resin has been obtained is less than 5% by weight In an advantageous embodiment, said initial reaction medium is heated for a time comprised from 20 minutes to 2 hours, in particular from approximately 30 minutes to approximately 1 hour, without removing the water present in the initial reaction medium as well as that formed, then the heating of said reaction medium is continued for 1 to 3 hours, while removing the water present in the reaction medium as well as that formed, in order to obtain a reaction medium containing a solid precursor, in the form of hard brittle resin.

In an advantageous embodiment, said initial reaction medium is heated for 1 hour 20 minutes to 5 hours, while removing the water present in the reaction medium as well as that formed, in order to obtain a reaction medium containing a solid precursor, in the form of hard brittle resin.

In an advantageous embodiment, the present invention relates to a process in which the water present in the initial reaction medium, as well as that produced during the reaction, are removed from said reaction medium during said heating and a solid precursor in the form of hard brittle resin, said solid precursor in the form of hard brittle resin being isolated from said reaction medium and not subjected to additional heat treatment.

In an advantageous embodiment, the present invention relates to a process in which the water present in the initial reaction medium, as well as that produced during the reaction, are removed from said reaction medium during said heating and a solid precursor in the form of hard brittle resin is obtained, said solid precursor in the form of hard brittle resin being isolated from the aforementioned reaction medium and devoid of additional heat treatment, said process comprising the following stages:

a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), in particular of formula (Ia), with aqueous formaldehyde, in order to constitute an initial reaction medium and heating of said initial reaction medium for a time comprised from 20 minutes to 2 hours, in particular from approximately 30 minutes to approximately 1 hour, while optionally removing the water present in the initial reaction medium as well as that formed, b. continuation of the heating of said reaction medium for 1 to 3 hours, while optionally removing the water present in the reaction medium as well as that formed, in order to obtain a reaction medium containing a solid precursor, in the form of hard brittle resin, said solid precursor in the form of hard brittle resin being isolated from said reaction medium, in order to obtain a mixture (b), comprising said large p-(R)calixarene or said mixture (a) of at least two of said large p-(R)calixarenes, said mixture (b) comprising in addition a mixture (c) of giant p-(R) calixarenes, the size of which is greater than 20, c. optionally, after neutralization of the base, at least one washing of said mixture (b) with a polar solvent, in particular methanol or acetonitrile, in order to obtain said mixture (b) in neutralized form, d. purification of said mixture (b), optionally neutralized, so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes.

e. optionally, purification of mixture (a) using GPC, by separating different fractions depending on their elution time, in order to obtain said large p-(R)calixarene.

In stage c., the neutralization can for example be carried out using an acid such as HCl or $H_2SO_4$, in particular HCl, diluted or not.

Stage e. can be carried out in order to separate said mixture (a) of at least two of said large p-(R)calixarenes into fractions of large p-(R)calixarenes of different size.

In an advantageous embodiment, the present invention relates to a process in which the water present in the initial reaction medium, as well as that produced during the reaction are removed from said reaction medium during said heating and a solid precursor in the form of an optionally isolated, hard brittle resin is obtained.

in which said solid precursor in the form of hard brittle resin, contained in said reaction medium, is placed in the presence of heat transfer means in the form of an oven, or of a heated liquid in which said solid precursor in the form of hard brittle resin is very slightly soluble or totally insoluble, in particular in toluene, xylene, a linear or branched alkane with a boiling point greater than 50° C., in particular greater than 100° C., in particular octane, or a silicone oil, and is subjected to an additional heat treatment.

The boiling point of said liquid is in particular greater than or equal to 110° C.

The additional heat treatment is carried out under reflux of said organic liquid, with or without stirring, preferably without stirring of the reaction medium.

The additional heat treatment is in particular carried out for a time comprised as a function of R and of the base from 3 to 24 hours and has in particular the effect on the one hand of completing the formation of the macrocycles, in particular those comprised in the solid precursor in the form of resin.

In a process according to the invention, said solid precursor in the form of hard brittle resin can optionally be subjected to an additional heat treatment, before optional neutralization, and purification.

In an advantageous embodiment, the present invention relates to a process comprising the following stages:
a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), in particular of formula (Ia),
   with aqueous formaldehyde, in order to constitute an initial reaction medium and heating of said initial reaction medium for a time comprised from 20 minutes to 2 hours, in particular from approximately 30 minutes to approximately 1 hour, while optionally removing the water present in the initial reaction medium as well as that formed,
b. continuation of the heating of said reaction medium for 1 to 3 hours, while optionally removing the water present in the reaction medium as well as that formed, in order to obtain a reaction medium containing a solid precursor, in the form of hard brittle resin,
c. optionally:
   heating of said reaction medium or said solid precursor using heat transmission means in the form of an oven, for 3 to 24 hours.
   or addition to said reaction medium or to said solid precursor in the form of hard brittle resin, of a liquid in which said solid precursor in the form of hard brittle resin is very slightly soluble or totally insoluble, in particular in toluene, xylene, a linear or branched alkane with a boiling point greater than 50° C., in particular greater than 100° C., in particular octane or a silicone oil, in order to obtain a reaction medium containing a solid in the form of hard brittle resin, and heating of said reaction medium containing a solid in the form of hard brittle resin, for 3 to 24 hours, with or without stirring.
   in order to obtain a mixture (b), comprising said large p-(R)calixarene or said mixture (a) of at least two of said large p-(R)calixarenes, said mixture (b) comprising in addition a mixture (c) of giant p-(R) calixarenes, the size of which is greater than 20,
d. optionally, after neutralization of the base, at least one washing of said mixture (b) with a polar solvent, in particular methanol or acetonitrile, in order to obtain said mixture (b) in neutralized form,
e. purification of said mixture (b), optionally neutralized, so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes.
f. optionally, purification of mixture (a) using GPC, by separating different fractions depending on their elution time, in order to obtain said large p-(R)calixarene.

In a process according to the invention, said solid precursor in the form of hard brittle resin is subjected to an additional heat treatment, before optional neutralization, and purification.

In an advantageous embodiment, the present invention relates to a process comprising the following stages:
a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), in particular of formula (Ia),
   with aqueous formaldehyde, in order to constitute an initial reaction medium and heating of said initial reaction medium for a time comprised from 20 minutes to 2 hours, in particular from approximately 30 minutes to approximately 1 hour, while optionally removing the water present in the initial reaction medium as well as that formed,
b. continuation of the heating of said reaction medium for 1 to 3 hours, while removing the water present in the reaction medium as well as that formed, in order to obtain a reaction medium containing a solid precursor, in the form of hard brittle resin,
c. heating of said reaction medium or said solid precursor using heat transmission means in the form of an oven, for 3 to 24 hours.
   or addition to said reaction medium or to said solid precursor in the form of hard brittle resin, of a liquid in which said solid precursor in the form of hard brittle resin is very slightly soluble or totally insoluble, in particular in toluene, xylene, a linear or branched alkane with a boiling point greater than 50° C., in particular greater than 100° C., in particular octane or a silicone oil, in order to obtain a reaction medium containing a solid in the form of hard brittle resin, and heating of said reaction medium containing a solid in the form of hard brittle resin, for 3 to 24 hours, with or without stirring,
   in order to obtain a mixture (b), comprising said large p-(R)calixarene or said mixture (a) of at least two of said large p-(R)calixarenes, said mixture (b) comprising in addition a mixture (c) of giant p-(R) calixarenes, the size of which is greater than 20,
d. optionally, after neutralization of the base, at least one washing of said mixture (b) with a polar solvent, in particular methanol or acetonitrile, in order to obtain said mixture (b) in neutralized form, e. purification of said mixture (b), optionally neutralized, so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes, f. optionally purification of mixture (a) using GPC, by separating different fractions depending on their elution time, in order to obtain said large p-(R)calixarene.

Advantageously, in stages a. and b., the heating is at approximately 110° C., 120° C., 130° C., 140° C., 150° C. or 160° C.

In particular, the additional heat treatment is carried out under reflux of said liquid, with or without stirring, preferably without stirring of the reaction medium.

The additional heat treatment makes it possible to complete the formation of the macrocycles.

Advantageously, the additional heat treatment is comprised from approximately 3 to 24 h.

Stage f. can be carried out in order to separate mixture (a) of at least two of said large p-(R)calixarenes into fractions of large p-(R)calixarenes of different size.

In an advantageous embodiment, the base used in stage a. is Ba(OH)$_2$, LiOH, KOH, NaOH, CsOH or RbOH and R represents benzyloxy.

In a process according to the invention, said solid precursor in the form of hard brittle resin is subjected to an additional heat treatment in an oven, before optional neutralization, and purification.

In an advantageous embodiment, the present invention relates to a process comprising the following stages:

a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), in particular of formula (Ia), with aqueous formaldehyde, in order to constitute an initial reaction medium and heating of said initial reaction medium for a time comprised from 20 minutes to 2 hours, in particular from approximately 30 minutes to approximately 1 hour, while optionally removing the water present in the initial reaction medium as well as that formed, b. continuation of the heating of said reaction medium for 1 to 3 hours, while removing the water present in the reaction medium as well as that formed, in order to obtain a reaction medium containing a solid precursor, in the form of hard brittle resin, c. heating of said reaction medium or said solid precursor using heat transmission means in the form of an oven, for 3 to 24 hours.

in order to obtain a mixture (b), comprising said large p-(R)calixarene or said mixture (a) of at least two of said large p-(R)calixarenes, said mixture (b) comprising in addition a mixture (c) of giant p-(R) calixarenes, the size of which is greater than 20, d. optionally, after neutralization of the base, at least one washing of said mixture (b) with a polar solvent, in particular methanol or acetonitrile, in order to obtain said mixture (b) in neutralized form, e. purification of said mixture (b), optionally neutralized, so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes.

f. optionally, purification of mixture (a) using GPC, by separating different fractions depending on their elution time, in order to obtain said large p-(R)calixarene.

In a process according to the invention, said solid precursor in the form of hard brittle resin is subjected to an additional heat treatment in a heated liquid, before optional neutralization, and purification.

In an advantageous embodiment, the present invention relates to a process comprising the following stages:

a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), in particular of formula (Ia), with aqueous formaldehyde, in order to constitute an initial reaction medium and heating of said initial reaction medium for a time comprised from 20 minutes to 2 hours, in particular from approximately 30 minutes to approximately 1 hour, while optionally removing the water present in the initial reaction medium as well as that formed, b. continuation of the heating of said reaction medium for 1 to 3 hours, while removing the water present in the reaction medium as well as that formed, in order to obtain a reaction medium containing a solid precursor, in the form of hard brittle resin, c. addition to said reaction medium or to said solid precursor in the form of hard brittle resin, of a liquid in which said solid precursor in the form of hard brittle resin is very slightly soluble or totally insoluble, in particular in toluene, xylene, a linear or branched alkane with a boiling point greater than 50° C., in particular greater than 100° C., in particular octane or a silicone oil, in order to obtain a reaction medium containing a solid in the form of hard brittle resin, and heating of said reaction medium containing a solid in the form of hard brittle resin, for 3 to 24 hours, with or without stirring, in order to obtain a mixture (b), comprising said large p-(R)calixarene or said mixture (a) of at least two of said large p-(R)calixarenes, said mixture (b) comprising in addition a mixture (c) of giant p-(R) calixarenes, the size of which is greater than 20, d. optionally, after neutralization of the base, at least one washing of said mixture (b) with a polar solvent, in particular methanol or acetonitrile, in order to obtain said mixture (b) in neutralized form, e. purification of said mixture (b), optionally neutralized, so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes, f. optionally, purification of mixture (a) using GPC, by separating different fractions depending on their elution time, in order to obtain said large p-(R)calixarene.

In the process according to the invention, the initial reaction medium comprises water, in particular contributed by the source of aqueous formaldehyde. Moreover, water forms during the reaction for the formation of calixarenes.

The water present in the initial reaction medium, as well as that produced during the reaction, can be retained in said reaction medium during said heating.

In an advantageous embodiment, the present invention relates to a process in which the water present in the initial reaction medium, as well as that produced during the reaction, are retained in the reaction medium during said heating and a solid precursor in the form of optionally isolated precipitate is obtained.

In this embodiment, the water present in the initial reaction medium, as well as that produced during the reaction are not removed but retained in the reaction medium.

As a result, the reaction medium does not solidify completely and a precipitate is obtained. The precipitate, in the same manner as the hard brittle resin, can be isolated by simple filtration.

In an advantageous embodiment, said initial reaction medium is heated for a time comprised from 20 minutes to 5 hours, in particular from approximately 30 minutes to approximately 2 hours.

In an advantageous embodiment, the present invention relates to a process in which the water present in the initial reaction medium, as well as that produced during the reaction, are retained in the reaction medium during said heating and a solid precursor in the form of precipitate is obtained, said solid precursor in the form of precipitate being isolated from the aforementioned reaction medium and not subjected to additional heat treatment, In an advantageous embodiment, the present invention relates to a process comprising the following stages:
a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), in particular of formula (Ia),
with aqueous formaldehyde, in order to constitute an initial reaction medium and heating of said initial reaction medium for a time comprised from 20 minutes to 5 hours, in particular from approximately 30 minutes to approximately 2 hours, without removing the water present in the initial reaction medium as well as that formed, in order to obtain a reaction medium containing a solid precursor, in the form of precipitate,
in order to obtain a mixture (b), comprising said large p-(R)calixarene or said mixture (a) of at least two of said large p-(R)calixarenes, said mixture (b) comprising in addition a mixture (c) of giant p-(R) calixarenes, the size of which is greater than 20,
b. optionally, after neutralization of the base, at least one washing of said mixture (b) with a polar solvent, in particular methanol or acetonitrile, in order to obtain said mixture (b) in neutralized form,
c. purification of said mixture (b), optionally neutralized, so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes.
d. optionally, purification of mixture (a) using GPC, by separating different fractions depending on their elution time, in order to obtain said large p-(R)calixarene.

In stage c., the neutralization can for example be carried out using an acid such as HCl or $H_2SO_4$, in particular HCl, diluted or not.

Stage d. can be carried out in order to separate said mixture (a) of at least two of said large p-(R)calixarenes into fractions of large p-(R)calixarenes of different size.

In an advantageous embodiment, the present invention relates to a process in which the water present in the initial reaction medium, as well as that produced during the reaction, are retained in the reaction medium during said heating and a solid precursor in the form of optionally isolated precipitate is obtained,
in which said solid precursor in the form of hard brittle resin, contained in said reaction medium, is placed in the presence of heat transfer means in the form of an oven, or of a heated liquid in which said solid precursor in the form of hard brittle resin is very slightly soluble or totally insoluble, in particular in toluene, xylene, a linear or branched alkane with a boiling point greater than 50° C., in particular greater than 100° C., in particular octane, or a silicone oil, and is subjected to an additional heat treatment.

The boiling point of said liquid is in particular greater than or equal to 110° C.

The additional heat treatment is in particular carried out under reflux of said liquid, with or without stirring, preferably without stirring of the reaction medium.

The additional heat treatment is in particular carried out for a time comprised as a function of R and of the base of 3 to 24 hours and has in particular the effect of completing the formation of the macrocycles, in particular those comprised in the solid precursor in the form of resin.

In a process according to the invention, said solid precursor in the form of precipitate can optionally be subjected to an additional heat treatment, before optional neutralization, and purification.

In an advantageous embodiment, the present invention relates to a process comprising the following stages:
a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), in particular of formula (Ia),
with aqueous formaldehyde, in order to constitute an initial reaction medium and heating of said initial reaction medium for a time comprised from 20 minutes to 5 hours, in particular from approximately 30 minutes to approximately 2 hours, without removing the water present in the initial reaction medium as well as that formed, in order to obtain a reaction medium containing a solid precursor, in the form of precipitate,
b. optionally, addition to said reaction medium or to said solid precursor in the form of precipitate of a liquid in which said solid precursor in the form of precipitate is very slightly soluble or totally insoluble, in particular in toluene, xylene, a linear or branched alkane with a boiling point greater than 50° C., in particular greater than 100° C., in particular octane or a silicone oil, in order to obtain a reaction medium containing a solid in the form of precipitate, and heating of said reaction medium containing a solid in the form of precipitate, for 3 to 24 hours, with or without stirring.
in order to obtain a mixture (b), comprising said large p-(R)calixarene or said mixture (a) of at least two of said large p-(R)calixarenes, said mixture (b) comprising in addition a mixture (c) of giant p-(R) calixarenes, the size of which is greater than 20,
c. optionally, after neutralization of the base, at least one washing of said mixture (b) with a polar solvent, in particular methanol or acetonitrile, in order to obtain said mixture (b) in neutralized form,
d. purification of said mixture (b), optionally neutralized, so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes,
e. optionally, purification of mixture (a) using GPC, by separating different fractions depending on their elution time, in order to obtain said large p-(R)calixarene.

In a process according to the invention, said solid precursor in the form of precipitate is subjected to an additional heat treatment, before optional neutralization, and purification.

In an advantageous embodiment, the present invention relates to a process comprising in particular the following stages:
a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), in particular of formula (Ia),
   with aqueous formaldehyde, in order to constitute an initial reaction medium and heating of said initial reaction medium for a time comprised from 20 minutes to 5 hours, in particular from approximately 30 minutes to approximately 2 hours, without removing the water present in the initial reaction medium as well as that formed, in order to obtain a reaction medium containing a solid precursor, in the form of precipitate,
b. addition to said reaction medium or to said solid precursor in the form of precipitate, of a liquid in which said solid precursor in the form of precipitate is very slightly soluble or totally insoluble, in particular in toluene, xylene, a linear or branched alkane with a boiling point greater than 50° C., in particular greater than 100° C., in particular octane or a silicone oil, in order to obtain a reaction medium containing a solid in the form of precipitate, and heating of said reaction medium containing a solid in the form of precipitate, for 3 to 24 hours, with or without stirring,
   in order to obtain a mixture (b), comprising said large p-(R)calixarene or said mixture (a) of at least two of said large p-(R)calixarenes, said mixture (b) comprising in addition a mixture (c) of giant p-(R) calixarenes, the size of which is greater than 20,
c. optionally, after neutralization of the base, at least one washing of said mixture (b) with a polar solvent, in particular methanol or acetonitrile, in order to obtain said mixture (b) in neutralized form,
d. purification of said mixture (b), optionally neutralized, so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes.
e. optionally, purification of mixture (a) using GPC, by separating different fractions depending on their elution time, in order to obtain said large p-(R)calixarene.

Advantageously, in stages a. and b., the heating is at approximately 110° C., 120° C., 130° C., 140° C., 150° C. or 160° C.

In particular, the additional heat treatment is carried out under reflux of said liquid, with or without stirring, preferably without stirring of the reaction medium.

The additional heat treatment makes it possible to complete the formation of the macrocycles.

Advantageously, the additional heat treatment is comprised from approximately 3 to 24 h.

Stage e. can be carried out in order to separate said mixture (a) of at least two of said large p-(R)calixarenes into fractions of large p-(R)calixarenes of different size.

In an advantageous embodiment, the base used in stage a. is $Ba(OH)_2$, LiOH, KOH, NaOH, CsOH or RbOH and R represents benzyloxy.

In a process according to the invention, the reaction medium comprises water and a liquid, said liquid being different from water.

In an advantageous embodiment, the present invention relates to a process in which said initial reaction medium also comprises a liquid, in particular an organic solvent, more particularly toluene, xylene, a linear or branched alkane having a boiling point greater than 50° C., in particular greater than 100° C., even more particularly octane or a silicone oil.

Advantageously, the heating is at approximately 110° C., 120° C., 130° C., 140° C., 150° C. or 160° C.

In an advantageous embodiment, said initial reaction medium is heated for a time comprised from 3 hours to 24 hours, removing the water present in the initial reaction medium as well as that formed.

In an advantageous embodiment, said initial reaction medium is heated for a time comprised from 3 hours to 24 hours, without removing the water present in the initial reaction medium as well as that formed.

In an advantageous embodiment, the present invention relates to a process comprising in particular the following stages:
a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), in particular of formula (Ia),
   with aqueous formaldehyde and a liquid, in particular an organic solvent, more particularly toluene, xylene, a linear or branched alkane having a boiling point greater than 50° C., in particular greater than 100° C., even more particularly octane or a silicone oil,
   in order to constitute an initial reaction medium, and heating of said initial reaction medium for a time comprised from 1 hour to 5 hours, in particular from approximately 1 hour to approximately 2 hours, without removing the water present in the initial reaction medium as well as that formed, in order to obtain a reaction medium containing a solid precursor, in the form of precipitate,
   in order to obtain a mixture (b), comprising said large p-(R)calixarene or said mixture (a) of at least two of said large p-(R)calixarenes, said mixture (b) comprising in addition a mixture (c) of giant p-(R) calixarenes, the size of which is greater than 20,
b. optionally, after neutralization of the base, at least one washing of said mixture (b) with a polar solvent, in particular methanol or acetonitrile, in order to obtain said mixture (b) in neutralized form,
c. purification of said mixture (b), optionally neutralized, so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes,
d. optionally purification of mixture (a) using GPC, by separating different fractions depending on their elution time, in order to obtain said large p-(R)calixarene.

In stage b., the neutralization can for example be carried out using an acid such as HCl or $H_2SO_4$, in particular HCl, diluted or not.

Stage d. can be carried out in order to separate mixture (a) of at least two of said large p-(R)calixarenes into fractions of large p-(R)calixarenes of different size.

In an advantageous embodiment, the present invention relates to a process in which said purification of said mixture (b) comprises a stage of recrystallization of said mixture (b) in order to obtain at the end of the recrystallization stage a precipitate and a filtrate, said filtrate comprising said large p-(R)calixarene or said mixture (a) of at least two of said large p-(R)calixarenes, devoid of said mixture (c) of giant p-(R)calixarenes, and the precipitate comprising said mixture (c) of giant p-(R)calixarenes, the size of which is greater than 20.

In an advantageous embodiment, the present invention relates to a process in which said purification of said mixture (b) comprises a stage of recrystallization with two solvents of said mixture (b) in order to obtain, after addition of the second solvent, a precipitate and a filtrate, said filtrate comprising said large p-(R)calixarene or said mixture (a) of at least two of said large p-(R)calixarenes, and mixture (c) of giant p-(R)calixarenes, and the precipitate comprising mainly calix[8]arene.

In the stage of recrystallization with two solvents, well known to a person skilled in the art, the first solvent is such that mixture (c) is soluble, hot, in said first solvent. The second solvent is such that mixture (c) is only slightly soluble or insoluble in said second solvent.

In a process according to the invention, said large p-(R)calixarene or said mixture (a) is obtained by dissolving mixture (b) in a minimum amount of a first solvent, hot, addition of a second solvent until a precipitate appears, immediate filtration, and after cooling of the filtrate previously obtained, second filtration in order to obtain a filtrate comprising said large p-(R)calixarene or said mixture (a), devoid of said mixture (c) of giant p-(R)calixarenes.

In an advantageous embodiment, the present invention relates to a process in which said purification of said mixture (b) comprises the following stages:
dissolving said mixture (b) in a minimum amount of a first solvent, hot, in order to obtain a hot solution of said mixture (b),
adding a second solvent to the hot solution of said mixture (b), until a precipitate appears, and immediate filtration, in order to obtain a filtrate containing the large calixarenes and the giant calixarenes,
after cooling of the filtrate obtained previously, filtration of said precipitate in order to obtain:
a filtrate comprising said large p-(R)calixarene or said mixture (a) of at least two of said large p-(R) calixarenes, devoid of said mixture (c) of giant p-(R)calixarenes, and
the isolated precipitate, comprising said mixture (c) of giant p-(R)calixarenes, the size of which is greater than 20.

In an advantageous embodiment, the present invention relates to a process in which said purification of said mixture (b) comprises the following stages:
dissolving said mixture (b) in a minimum amount of a first solvent, hot, in order to obtain a hot solution of said mixture (b),
adding a second solvent to the hot solution of said mixture (b), until a first precipitate appears,
hot filtration of said first precipitate in order to obtain a filtrate,
cooling of the filtrate in order to obtain the formation of a second precipitate,
filtration of said second precipitate in order to obtain:
a filtrate comprising said large p-(R)calixarene or said mixture (a) of at least two of said large p-(R) calixarenes, devoid of said mixture (c) of giant p-(R)calixarenes, and
the isolated precipitate, comprising said mixture (c) of giant p-(R)calixarenes, the size of which is greater than 20.

In a process according to the invention, said large p-(R) calixarene or said mixture (a) is obtained by dissolving mixture (b) in a minimum amount of a first solvent, hot, addition of a second solvent until a precipitate appears, immediate hot filtration, cooling of the filtrate then appearance of a precipitate, fresh filtration and concentration of the filtrate in order to obtain said large p-(R)calixarene or said mixture (a), devoid of said mixture (c) of giant p-(R) calixarenes.

In an advantageous embodiment, the present invention relates to a process in which said purification of said mixture (b) comprises the following stages:
dissolving said mixture (b) in a minimum amount of a first solvent, hot, in order to obtain a hot solution of said mixture (b),
adding a second solvent to the hot solution of said mixture (b), until a first precipitate appears,
hot filtration of said first precipitate in order to obtain a filtrate,
cooling of the filtrate in order to obtain the formation of a second precipitate,
filtration of said second precipitate in order to obtain:
a filtrate comprising said large p-(R)calixarene or said mixture (a) of at least two of said large p-(R) calixarenes, devoid of said mixture (c) of giant p-(R)calixarenes, and
the isolated precipitate, comprising said mixture (c) of giant p-(R)calixarenes, the size of which is greater than 20,
concentration of said filtrate in order to obtain said large p-(R)calixarene or said mixture (a) of at least two of said large p-(R)calixarenes, devoid of said mixture (c) of giant p-(R)calixarenes.

In a process according to the invention, said large p-(R) calixarene or said mixture (a) is obtained by dissolving mixture (b) in a minimum amount of DMSO, hot, addition of a second, averagely polar solvent, in particular acetone, until a precipitate appears, immediate hot filtration, cooling of the filtrate then appearance of a precipitate, fresh filtration and concentration of the filtrate in order to obtain said large p-(R)calixarene or said mixture (a), devoid of said mixture (c) of giant p-(R)calixarenes.

In an advantageous embodiment, the present invention relates to a process in which said purification of said mixture (b) comprises the following stages:
dissolving said mixture (b) in a minimum amount of DMSO, at a temperature comprised from approximately 80° C. to approximately 160° C., in particular from approximately 100° C. to approximately 140° C., more particularly at a temperature of approximately 120° C., in order to obtain a hot solution of said mixture (b),
adding a second, averagely polar solvent, in particular acetone, to the hot solution of said mixture (b), until a first precipitate appears,
hot filtration of said first precipitate in order to obtain a filtrate, cooling of the filtrate to approximately 0° C. in order to obtain the formation of a second precipitate, filtration of said second precipitate in order to obtain:
- a filtrate comprising said large p-(R)calixarene or said mixture (a) of at least two of said large p-(R) calixarenes, devoid of said mixture (c) of giant p-(R)calixarenes, and
- the isolated precipitate, comprising said mixture (c) of giant p-(R)calixarenes, the size of which is greater than 20.

concentration of said filtrate in order to obtain said large p-(R)calixarene or said mixture (a) of at least two of said large p-(R)calixarenes, devoid of said mixture (c) of giant p-(R)calixarenes.

By averagely polar solvent is meant a solvent having a dielectric constant comprised between 5 and 25.

In an advantageous embodiment, the present invention relates to a process in which said purification of said mixture (b) comprises the following stages:

dissolving said mixture (b) in a minimum amount of DMSO, at a temperature comprised from approximately 80° C. to approximately 160° C., in particular from approximately 100° C. to approximately 140° C., more particularly at a temperature of approximately 120° C., in order to obtain a hot solution of said mixture (b), adding a second, averagely polar solvent, in particular acetone, to the hot solution of said mixture (b), until a first precipitate appears, hot filtration of said first precipitate in order to obtain a filtrate, cooling of the filtrate to approximately 0° C. in order to obtain the formation of a second precipitate, filtration of said second precipitate in order to obtain:
- a filtrate comprising said large p-(R)calixarene or said mixture (a) of at least two of said large p-(R) calixarenes, devoid of said mixture (c) of giant p-(R)calixarenes, and
- the isolated precipitate, comprising said mixture (c) of giant p-(R)calixarenes, the size of which is greater than 20, concentration of said filtrate in order to obtain a residue devoid of acetone, addition to said residue of a polar solvent, in particular ethanol, in particular at ambient temperature, in order to obtain a solution of said residue in said polar solvent, cooling of said solution of said residue, in particular to approximately 0°, in order to obtain a suspension, said suspension being filtered in order to obtain a filtrate, said filtrate being concentrated in order to obtain said large p-(R)calixarene or said mixture (a) of at least two of said large p-(R)calixarenes, devoid of said mixture (c) of giant p-(R)calixarenes.

EXAMPLES

Example 1: Synthesis of Large Calixarenes, with Additional Heat Treatment in a Silicone Oil 104 g de p-(benzyloxy)phenol, 133 ml of formaldehyde in aqueous solution at 37%, and 36 ml of CsOH in aqueous solution at 50% are introduced into a 2-liter three-necked flask equipped with a mechanical stirrer.

The resulting white suspension is brought to reflux under vigorous stirring.

After approximately 30 minutes of reflux, a clear bright yellow solution is obtained.

Vigorous argon flushing is introduced in the flask, in order to remove the water. The solution is thus progressively concentrated, until a hard brittle solid material is obtained.

Then, 280 ml of silicone oil is added under argon and the heterogeneous reaction medium thus obtained is heated at 145° C. under argon flushing for 24 hours. No solubilization/evolution of solid is observed during this time.

The silicone oil is removed by filtration. The yellow solid is then washed with 1 L of pentane under vigorous mechanical stirring. Then, it is dispersed in 1.5 l of MeOH under vigorous stirring. 40 ml of HCl at 37% is added to the fluid suspension thus obtained. The resulting precipitate is recovered by filtration, then dried in air.

This precipitate is suspended in 1.5 l of acetonitrile under vigorous stirring overnight. The resulting fluid suspension is filtered, and the precipitate obtained recrystallized in a DMSO/acetone mixture (1/9) and filtered hot. After storing the filtrate in a refrigerator (1° C.) for 48 hours, 60 g of a precipitate constituted by giant calixarenes is obtained.

The corresponding filtrate is concentrated in a rotary evaporator (removal of the acetone), and 20 ml of ethanol is added.

The clear solution thus obtained is stored in a refrigerator (1° C.) for 48 hours. The suspension obtained is filtered.

The corresponding filtrate is concentrated in a rotary evaporator and precipitated with 1 L of methanol.

After filtration, 25 g of a mixture containing "large" calixarenes is thus obtained.

Example 2: Synthesis of Large Calixarenes, with Heat Treatment in Xylene 104 g de p-(benzyloxy)phenol, 140 ml of formaldehyde in aqueous solution at 37%, and 72 ml of CsOH in aqueous solution at 50% are introduced into a 2-liter three-necked flask equipped with a mechanical stirrer.

The resulting white suspension is brought to reflux under vigorous stirring.

After approximately 30 minutes of reflux, a clear bright yellow solution is obtained.

Vigorous argon flushing is introduced in the flask, in order to remove the water. The solution is thus progressively concentrated, until a hard brittle solid material is obtained.

Then, 200 ml of xylene is added under argon and the heterogeneous reaction medium thus obtained is brought to reflux at 145° C. without stirring for 5 hours.

The yellow solid obtained is then neutralized with a mixture of 500 ml of THF and 50 ml of HCl at 37%, under vigorous stirring for one day.

The suspension is evaporated to dryness, then washed with 1.2 L of MeOH under vigorous stirring overnight, then filtered. The precipitate obtained is suspended in 1.5 l of acetonitrile under vigorous stirring overnight. The resulting fluid suspension is filtered, and the precipitate obtained recrystallized in a DMSO/acetone mixture (175 ml/2 L) and filtered hot. After storing the filtrate in a refrigerator (1° C.) for 48 hours, 20 g of a precipitate constituted by giant calixarenes is obtained.

The corresponding filtrate is concentrated in a rotary evaporator (removal of the acetone), and 20 ml of ethanol is added.

The clear solution thus obtained is stored in a refrigerator (1° C.) for 48 hours. The suspension obtained is filtered.

The corresponding filtrate is concentrated in a rotary evaporator and precipitated with 1 L of methanol.

After filtration, 56 g of a mixture comprising "large" calixarenes is thus obtained.

Example 3: Synthesis of Large Calixarenes, with Heat Treatment in Xylene 104 g de p-(benzyloxy)phenol, 140 ml of formaldehyde in aqueous solution at 37%, and 50 ml of RbOH in aqueous solution at 50% are introduced into a 2-liter three-necked flask equipped with a mechanical stirrer.

The resulting white suspension is brought to reflux under vigorous stirring.

After approximately 30 minutes of reflux, a clear bright yellow solution is obtained.

Vigorous argon flushing is introduced in the flask, in order to remove the water. The solution is thus progressively concentrated, until a hard brittle solid material is obtained.

Then, 200 ml of xylene is added under argon and the heterogeneous reaction medium thus obtained is brought to reflux at 145° C. without stirring for 7 hours 30 minutes.

The yellow solid obtained is then neutralized with a mixture of 500 ml of THF and 50 ml of HCl at 37%, under vigorous stirring for one day.

The suspension obtained is evaporated to dryness, then washed with 2 L of MeOH under vigorous stirring overnight, then filtered. The precipitate obtained is suspended in 1 L of acetonitrile under vigorous stirring overnight. The resulting fluid suspension is filtered, and the precipitate obtained recrystallized in a DMSO/acetone mixture (200 ml/2 L) and filtered hot.

After storing the filtrate in a refrigerator (1° C.) for 48 hours, 20 g of a precipitate constituted by giant calixarenes is obtained.

The corresponding filtrate is concentrated in a rotary evaporator (removal of the acetone), and 20 ml of ethanol is added.

The clear solution thus obtained is stored in a refrigerator (1° C.) for 24 hours. The suspension obtained is filtered.

The corresponding filtrate is concentrated in a rotary evaporator and precipitated with 1 L of methanol.

After filtration, 30 g of a mixture containing "large" calixarenes is thus obtained.

Example 4: Synthesis of a Star Polymer Derived from a Large Calixarene

Synthesis of the Initiator

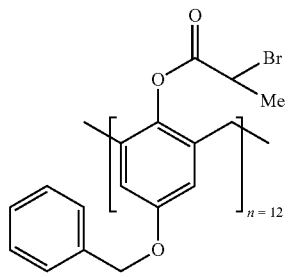

A large calixarene, here calix[12]arene (500 mg, 0.0002 mol), is introduced into a Schlenk tube. 5 mL of DMF and 1.5 mL of Et$_3$N are then added under argon. The system is immersed in an ice bath. Then 300 µL of bromopropionyl bromide is introduced. The solution is stirred for 1 h. A precipitation is carried out from 50 mL of MeOH. Filtration under vacuum is carried out. The initiator is solubilized in a few milliliters of THF. Then a second precipitation is carried out with 50 mL of MeOH. Filtration under vacuum is carried out. The product is dried in a desiccator.

Yield=60%.

RMN$^1$H (350 MHz, CDCl3) $\delta_{ppm}$: 7.1-7.6 (m, 60H, —OCH$_2$—Ar), 6.8-6.4 (m, 24H, Ar), 5.1-4.7 (m, 24H, —OCH$_2$—Ar—), 4-3.5 (m, 24H, —Ar(phenol)-CH$_2$—), 3-1.5 (m, 24H, CH$_3$—CH(COR)—Br), 2-1.5 (m, 36H, CH$_3$—CH(COR)—Br).

Synthesis of the Star Polymer by Atom Transfer Radical Polymerization (ATRP)

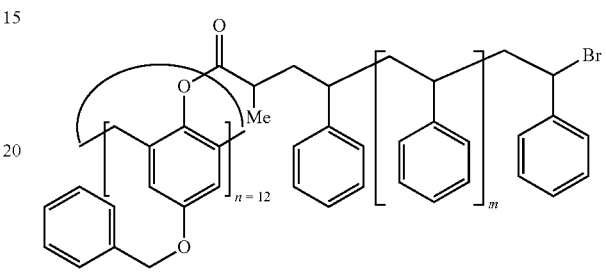

CuBr (25 mg, 0.00017 mol), bipyridine (80 mg, 0.00052 mol), the initiator obtained previously (60 mg, 0.00017 mol) and 2 mL of styrene are introduced into a Schlenk tube under argon. The reaction medium is degassed using 3 freeze-thaw cycles. The Schlenk tube is immersed in an oil bath heated at 100° C. for a given period of time. The mixture is solubilized in THF. The mixture is filtered on a column of basic Al$_2$O$_3$. The polymer is precipitated from MeOH $$\left(\text{with a ratio} = \frac{\text{THF}}{\text{MeOH}} = 10\right).$$

The polymer is filtered under vacuum and rinsed with MeOH. The product is dried in a desiccator.

Yield=50%.

RMN$^1$H (360 MHz, CDCl3) $\delta_{ppm}$: 7.1-7.6 (m, 5H, —OCH$_2$—Ar), 7.2-6.9 (m, 5H, Ar$_{styrene}$), 7.2-6.9 (m, 1H, —CH$_2$—CH(Ar)—CH$_2$—), 6.8-6.4 (m, 2H, Ar), 2.1-1.6 (m, 2H, —CH—CH$_2$—CH—), 2.1-1.6 (m, 1H, HO$_2$C—CH(CH$_3$)—CH$_2$—), 1.6-1.3 (m, 3H, CH$_3$—CH—).

The star polymers derived from the calix[12]arene exhibit specific "hard sphere"-type hydrodynamic behaviour, and therefore form well-defined nanoobjects in solution (THF), which are potentially useful for encapsulation and vectorization.

The invention claimed is:
1. A process for preparing:
a large p-(R)calixarene selected from the group consisting of a p-(R)calix[9]arene, a p-(R)calix[10]arene, a p-(R)calix[11]arene, a p-(R)calix[12]arene, a p-(R)calix[13]arene, a p-(R)calix[14]arene, a p-(R)calix[15]arene, a p-(R)calix[16]arene, a p-(R)calix[17]arene, a p-(R)calix[18]arene, a p-(R)calix[19]arene, and a p-(R)calix[20]arene, or
a mixture of at least two of said large p-(R)calixarenes in which said at least two large p-(R)calixarenes are present in said mixture each at a level of at least 5 mol. %, said process comprising:
bringing at least one base selected from the group consisting of barium hydroxide, rubidium hydroxide, lithium hydroxide, caesium hydroxide, potassium hydroxide and sodium hydroxide, into contact with at least one phenol substituted in position 4 of the following formula (I):

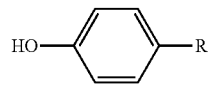
(I)

in which R is selected from:
  a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
  a linear or branched $C_1$-$C_{20}$ alkyl group, with the exclusion of the t-butyl group,
  a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
  a linear or branched $C_1$-$C_{20}$ alkyloxy group,
  a linear or branched 1 to 10 O-PEG group, the —OH end group of which is alkylated with a linear or branched $C_1$-$C_{20}$ alkyl,
  a benzyl thioether group —S—$CH_2$-Ph optionally substituted in the ortho and/or para and/or meta position with one or more substituents selected from a halogen, SR' and OR', $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
  a linear or branched $C_1$-$C_{20}$ alkyl thioether group, of formula —S—($C_1$-$C_{20}$-alkyl),
  an —$NR_aR_b$ group, $R_a$ and $R_b$ representing, independently of one another, a linear or branched $C_1$-$C_{20}$ alkyl, and
  a dibenzylamine group of formula —N(benzyl)$_2$, in which the two benzyl groups are, independently of one another, optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
and a source of aqueous formaldehyde, in the absence of an organic solvent, thus constituting an initial reaction medium, said base being at a total concentration comprised from approximately 0.01 to 1 equivalent, with respect to said at least one phenol substituted in position 4 of formula (I), said initial reaction medium being heated to a temperature comprised from 100 to 165° C., in order to obtain a heated reaction medium;

optionally, after said heating, additional heat treating of said heated reaction medium, in the presence of heat transfer means, in order to obtain a mixture (b), comprising said large p-(R)calixarene or said mixture (a) of at least two of said large p-(R)calixarenes, said mixture (b) comprising in addition a mixture (c) of giant p-(R)calixarenes, the size of which is greater than 20; and after said heating and optional additional heat treating, purifying said mixture (b), so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes.

2. The process according to claim 1, for the preparation of:
  a large p-(R)calixarene selected from the group consisting of a p-(R)calix[9]arene, a p-(R)calix[10]arene, a p-(R)calix[11]arene, and a p-(R)calix[12]arene, or
  a mixture of at least two of said large p-(R)calixarenes in which said at least two large p-(R)calixarenes are present in said mixture each at a level of at least 5 mol. %.

3. The process according to claim 1, for the preparation of:
  a large p-($R_1$-oxy)calixarene selected from the group consisting of a p-($R_1$-oxy)calix[9]arene, a p-($R_1$-oxy)calix[10]arene, a p-($R_1$-oxy)calix[11]arene, a p-($R_1$-oxy)calix[12]arene, a p-($R_1$-oxy)calix[13]arene, a p-($R_1$-oxy)calix[14]arene, a p-($R_1$-oxy)calix[15]arene, a p-($R_1$-oxy)calix[16]arene, a p-($R_1$-oxy)calix[17]arene, a p-($R_1$-oxy)calix[18]arene, a p-($R_1$-oxy)calix[19]arene, and a p-($R_1$-oxy)calix[20]arene, or
  a mixture of at least two of said large p-($R_1$-oxy)calixarenes in which said at least two large p-($R_1$-oxy)calixarenes are present in said mixture each at a level of at least 5 mol. %,
said process comprising:
bringing at least one base selected from the group consisting of barium hydroxide, rubidium hydroxide, lithium hydroxide, caesium hydroxide, potassium hydroxide and sodium hydroxide, into contact with at least one phenol substituted in position 4 of the following formula (Ia):

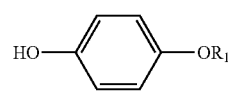
(Ia)

in which $R_1$ is selected from:
a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyl group, and
a linear or branched PEG 1 to 10, the —OH end group of which is alkylated with a linear or branched $C_1$-$C_{20}$ alkyl,
and a source of aqueous formaldehyde, in the absence of an organic solvent, thus constituting an initial reaction medium, said base being at a total concentration comprised from approximately 0.01 to 1 equivalent, with respect to said at least one phenol substituted in position 4 of formula (I), said initial reaction medium being heated to a temperature comprised from 100 to 165° C., in order to obtain a heated reaction medium;

optionally, after said heating, additional heat treating of said heated reaction medium, in the presence of heat transfer means, in order to obtain a mixture (b), comprising said large p-($R_1$-oxy)calixarene or said mixture (a) of at least two of said large p-($R_1$-oxy)calixarenes, said mixture (b) comprising in addition a mixture (c) of giant p-($R_1$-oxy)calixarenes, the size of which is greater than 20; and after said heating and optional additional heat treating, purifying said mixture (b), so as to remove said mixture (c) of giant p-($R_1$-oxy)calixarenes, and to obtain said large p-($R_1$-oxy)calixarene or said mixture (a) of at least two of said large p-($R_1$-oxy)calixarenes, devoid of said mixture (c) of giant p-($R_1$-oxy)calixarenes.

4. The process according to claim 1, for preparing:
a large p-($R_1$-oxy)calixarene selected from the group consisting of a p-($R_1$-oxy)calix[9]arene, a p-($R_1$-oxy)calix[10]arene, a p-($R_1$-oxy)calix[11]arene, and a p-($R_1$-oxy)calix[12]arene, or
a mixture of at least two of said large p-($R_1$-oxy)calixarenes in which said at least two large p-($R_1$-oxy)calixarenes are present in said mixture each at a level of at least 5 mol. %.

5. The process according to claim 1, in which water present in the initial reaction medium, as well as that produced during the reaction, is removed from said reaction medium during said heating and a solid precursor in the form of optionally isolated hard brittle resin is obtained, wherein:
said solid precursor in the form of hard brittle resin is isolated from the of reaction medium and not subjected to said additional heat treating, or
said solid precursor in the form of hard brittle resin, contained in said reaction medium, is placed in the presence of heat transfer means in the form of an oven, or of a heated liquid in which said solid precursor in the form of hard brittle resin is very slightly soluble or totally insoluble in toluene, xylene, a linear or branched alkane with a boiling point greater than 50° C., or a silicone oil, and is subjected to said additional heat treating.

6. The process according to claim 1, comprising the steps of:
a. bringing at least one base, selected from the group consisting of barium hydroxide, rubidium hydroxide, lithium hydroxide, caesium hydroxide, potassium hydroxide and sodium hydroxide, into contact with at least one phenol substituted in position 4 of formula (I), with aqueous formaldehyde, in order to constitute an initial reaction medium and heating of said initial reaction medium for a time comprised from 20 minutes to 2 hours, while optionally removing the water present in the initial reaction medium as well as that formed,
b. continuing the heating of said reaction medium for 1 to 3 hours, while optionally removing the water present in the reaction medium as well as that formed, in order to obtain a reaction medium containing a solid precursor, in the form of hard brittle resin,
c. heating of said reaction medium or said solid precursor using heat transmission means in the form of an oven, for 3 to 24 hours, or adding to said reaction medium or to said solid precursor in the form of hard brittle resin, a liquid in which said solid precursor in the form of hard brittle resin is very slightly soluble or totally insoluble in toluene, xylene, a linear or branched alkane with a boiling point greater than 50° C., or a silicone oil, in order to obtain a reaction medium containing a solid in the form of hard brittle resin, and heating of said reaction medium containing a solid in the form of hard brittle resin, for 3 to 24 hours, with or without stirring, in order to obtain a mixture (b), comprising said large p-(R)calixarene or said mixture (a) of at least two of said large p-(R)calixarenes, said mixture (b) comprising in addition a mixture (c) of giant p-(R) calixarenes, the size of which is greater than 20,
d. optionally, after neutralizing the base, at least one washing of said mixture (b) with a polar solvent, in order to obtain said mixture (b) in neutralized form,
e. purifying said mixture (b), optionally neutralized, so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes,
f. optionally, purifying mixture (a) using GPC, by separating different fractions depending on their elution time, in order to obtain said large p-(R)calixarene.

7. The process according to claim 1, in which the water present in the initial reaction medium, as well as that produced during the reaction, are retained in the reaction medium during said heating and a solid precursor in the form of optionally isolated precipitate is obtained, wherein said solid precursor in the form of precipitate is isolated from the aforesaid reaction medium and not subjected to additional heat treatment.

8. The process according to claim 7, in which the water present in the initial reaction medium, as well as that produced during the reaction, are retained in said reaction medium during said heating and a solid precursor in the form of optionally isolated precipitate is obtained, wherein said solid precursor in the form of precipitate is isolated from the aforesaid reaction medium and not subjected to additional heat treatment.

9. The process according to claim 1, in which said purifying said mixture (b) comprises recrystallizing of said mixture (b) in order to obtain at the end of the recrystallizing a precipitate and a filtrate, said filtrate comprising said large p-(R)calixarene or said mixture (a) of at least two of said large p-(R)calixarenes, devoid of said mixture (c) of giant p-(R)calixarenes, and the precipitate comprising said mixture (c) of giant p-(R)calixarenes, the size of which is greater than 20.

10. The process according to claim 1, in which said purifying of said mixture (b) comprises a recrystallizing with two solvents of said mixture (b) in order to obtain, after adding the second solvent, a precipitate and a filtrate, said filtrate comprising said large p-(R)calixarene or said mixture (a) of at least two of said large p-(R)calixarenes, and mixture (c) of giant p-(R)calixarenes, and the precipitate comprising mainly calix[8]arene.

11. The process according to claim 1, in which said purifying of said mixture (b) comprises the steps of:
dissolving said mixture (b) in a minimum amount of a first solvent, hot, in order to obtain a hot solution of said mixture (b),
adding a second solvent to the hot solution of said mixture (b), until a precipitate appears, and immediate filtration, in order to obtain a filtrate containing the large calixarenes and the giant calixarenes,
after cooling of the filtrate obtained previously, filtration of said precipitate in order to obtain:

a filtrate comprising said large p-(R)calixarene or said mixture (a) of at least two of said large p-(R) calixarenes, devoid of said mixture (c) of giant p-(R)calixarenes, and the isolated precipitate, comprising said mixture (c) of giant p-(R)calixarenes, the size of which is greater than 20.

12. The process according to claim 1, in which said purifying of said mixture (b) comprises the steps of:
dissolving said mixture (b) in a minimum amount of a first solvent, hot, in order to obtain a hot solution of said mixture (b),
adding a second solvent to the hot solution of said mixture (b), until a first precipitate appears,
hot filtering of said first precipitate in order to obtain a filtrate,
cooling of the filtrate in order to obtain the formation of a second precipitate,
filtering of said second precipitate in order to obtain:
a filtrate comprising said large p-(R)calixarene or said mixture (a) of at least two of said large p-(R) calixarenes, devoid of said mixture (c) of giant p-(R)calixarenes, and
the isolated precipitate, comprising said mixture (c) of giant p-(R)calixarenes, the size of which is greater than 20.

13. The process according to claim 1, in which said purifying of said mixture (b) comprises the steps of:
dissolving said mixture (b) in a minimum amount of DMSO, at a temperature comprised from approximately 80° C. to approximately 160° C., in order to obtain a hot solution of said mixture (b),
adding a second, averagely polar solvent, in particular acetone, to the hot solution of said mixture (b), until a first precipitate appears,
hot filtering of said first precipitate in order to obtain a filtrate,
cooling of the filtrate to approximately 0° C. in order to obtain the formation of a second precipitate,
filtering of said second precipitate in order to obtain:
a filtrate comprising said large p-(R)calixarene or said mixture (a) of at least two of said large p-(R) calixarenes, devoid of said mixture (c) of giant p-(R)calixarenes, and
the isolated precipitate, comprising said mixture (c) of giant p-(R)calixarenes, the size of which is greater than 20,
concentrating said filtrate in order to obtain said large p-(R)calixarene or said mixture (a) of at least two of said large p-(R)calixarenes, devoid of said mixture (c) of giant p-(R)calixarenes.

14. The process according to claim 1, in which said purifying of said mixture (b) comprises the steps of:
dissolving said mixture (b) in a minimum amount of DMSO, at a temperature comprised from approximately 80° C. to approximately 160° C., in order to obtain a hot solution of said mixture (b),
adding a second, averagely polar solvent, in particular acetone, to the hot solution of said mixture (b), until a first precipitate appears,
hot filtering of said first precipitate in order to obtain a filtrate,
cooling of the filtrate to approximately 0° C. in order to obtain the formation of a second precipitate,
filtering of said second precipitate in order to obtain:
a filtrate comprising said large p-(R)calixarene or said mixture (a) of at least two of said large p-(R) calixarenes, devoid of said mixture (c) of giant p-(R)calixarenes, and
the isolated precipitate, comprising said mixture (c) of giant p-(R)calixarenes, the size of which is greater than 20,
concentrating of said filtrate in order to obtain a residue devoid of acetone,
adding to said residue of a polar solvent, in order to obtain a solution of said residue in said polar solvent,
cooling of said solution of said residue, in order to obtain a suspension, said suspension being filtered in order to obtain a filtrate, said filtrate being concentrated in order to obtain said large p-(R)calixarene or said mixture (a) of at least two of said large p-(R)calixarenes, devoid of said mixture (c) of giant p-(R)calixarenes.

15. The process according to claim 1, wherein water present in the initial reaction medium, as well as that produced during the reaction, is removed from said reaction medium during said heating and a solid precursor in the form of optionally isolated hard brittle resin is obtained, and said process comprises the steps of:
bringing at least one base selected from the group consisting of barium hydroxide, rubidium hydroxide, lithium hydroxide, caesium hydroxide, potassium hydroxide and sodium hydroxide, into contact with at least one phenol substituted in position 4 of formula (I), with aqueous formaldehyde, in order to constitute an initial reaction medium, and heating of said initial reaction medium for a time comprised from 20 minutes to 2 hours, while optionally removing the water present in the initial reaction medium as well as that formed,
continuing the heating of said reaction medium for 1 to 3 hours, while optionally removing the water present in the reaction medium as well as that formed, in order to obtain a reaction medium containing a solid precursor, in the form of hard brittle resin,
optionally:
heating of said reaction medium or said solid precursor using heat transmission means in the form of an oven, for 3 to 24 hours,
adding to said reaction medium or to said solid precursor in the form of hard brittle resin, a liquid in which said solid precursor in the form of hard brittle resin is very slightly soluble or totally insoluble in toluene, xylene, a linear or branched alkane with a boiling point greater than 50° C., or a silicone oil, in order to obtain a reaction medium containing a solid in the form of hard brittle resin, and heating of said reaction medium containing a solid in the form of hard brittle resin, for 3 to 24 hours, with or without stirring, in order to obtain a mixture (b), comprising said large p-(R)calixarene or said mixture (a) of at least two of said large p-(R)calixarenes, said mixture (b) comprising in addition a mixture (c) of giant p-(R)calixarenes, the size of which is greater than 20,
optionally, after neutralizing the base, at least one washing of said mixture (b) with a polar solvent, in order to obtain said mixture (b) in neutralized form,
purifying said mixture (b), optionally neutralized, so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes, and optionally purifying said mixture (a) using GPC, by separating different fractions depending on their elution time, in order to obtain said large p-(R)calixarene.

16. The process according to claim 1, wherein the water present in the initial reaction medium, as well as that produced during the reaction, are retained in the reaction medium during said heating and a solid precursor in the form of optionally isolated precipitate is obtained, and said process comprises the steps of:
bringing at least one base, selected from the group consisting of barium hydroxide, rubidium hydroxide, lithium hydroxide, caesium hydroxide, potassium hydroxide and sodium hydroxide, into contact with at least one phenol substituted in position 4 of formula (I), with aqueous formaldehyde, in order to constitute an initial reaction medium and heating of said initial reaction medium for a time comprised from 20 minutes to 5 hours, without removing the water present in the initial reaction medium as well as that formed, in order to obtain a reaction medium containing a solid precursor, in the form of precipitate,
optionally, adding to said reaction medium or to said solid precursor in the form of precipitate, a liquid in which said solid precursor in the form of precipitate is very slightly soluble or totally insoluble in toluene, xylene, a linear or branched alkane with a boiling point greater than 50° C., or a silicone oil, in order to obtain a reaction medium containing a solid in the form of precipitate, and heating of said reaction medium containing a solid in the form of precipitate, for 3 to 24 hours, with or without stirring, in order to obtain a mixture (b), comprising said large p-(R)calixarene or said mixture (a) of at least two of said large p-(R)calixarenes, said mixture (b) comprising in addition a mixture (c) of giant p-(R)calixarenes, the size of which is greater than 20,
optionally, after neutralizing the base, at least one washing of said mixture (b) with a polar solvent, in order to obtain said mixture (b) in neutralized form,
purifying said mixture (b), optionally neutralized, so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes, and
optionally, purifying mixture (a) using GPC, by separating different fractions depending on their elution time, in order to obtain said large p-(R)calixarene.

17. The process according to claim 16, comprising the steps of:
bringing at least one base, selected from the group consisting of barium hydroxide, rubidium hydroxide, lithium hydroxide, caesium hydroxide, potassium hydroxide and sodium hydroxide, into contact with at least one phenol substituted in position 4 of formula (I), with aqueous formaldehyde, in order to constitute an initial reaction medium and heating of said initial reaction medium for a time comprised from 20 minutes to 5 hours, without removing the water present in the initial reaction medium as well as that formed, in order to obtain a reaction medium containing a solid precursor, in the form of precipitate,
adding to said reaction medium or to said solid precursor in the form of precipitate, a liquid in which said solid precursor in the form of precipitate is very slightly soluble or totally insoluble in toluene, xylene, a linear or branched alkane with a boiling point greater than 50° C., or a silicone oil, in order to obtain a reaction medium containing a solid in the form of precipitate, and heating of said reaction medium containing a solid in the form of precipitate, for 3 to 24 hours, with or without stirring, in order to obtain a mixture (b), comprising said large p-(R)calixarene or said mixture (a) of at least two of said large p-(R)calixarenes, said mixture (b) comprising in addition a mixture (c) of giant p-(R)calixarenes, the size of which is greater than 20,
optionally, after neutralizing the base, at least one washing of said mixture (b) with a polar solvent, in order to obtain said mixture (b) in neutralized form,
purifying said mixture (b), optionally neutralized, so as to remove said mixture (c) of giant p-(R)calixarenes, and to obtain said large p-(R)calixarene or said mixture (a) of at least two of said large p-(R)calixarenes, devoid of said mixture (c) of giant p-(R)calixarenes, and
optionally purifying of mixture (a) using GPC, by separating different fractions depending on their elution time, in order to obtain said large p-(R)calixarene.

* * * * *